United States Patent [19]

Kotwal et al.

[11] Patent Number: 5,474,786
[45] Date of Patent: Dec. 12, 1995

[54] MULTILAYERED CONTROLLED RELEASE PHARMACEUTICAL DOSAGE FORM

[75] Inventors: Pramod M. Kotwal, Blue Bell, Pa.; Stephen A. Howard, Flemington, N.J.

[73] Assignee: Ortho Pharmaceutical Corporation, Raritan, N.J.

[21] Appl. No.: 319,186

[22] Filed: Oct. 6, 1994

Related U.S. Application Data

[62] Division of Ser. No. 217,331, Mar. 23, 1994, Pat. No. 5,395,626.

[51] Int. Cl.⁶ .................. A61K 9/54; A61K 9/62
[52] U.S. Cl. ............. 424/472; 424/458; 424/461; 424/462; 424/469; 424/488; 424/490; 424/494; 424/495; 424/497
[58] Field of Search .................... 424/490, 494, 424/495, 497, 488, 469, 472, 458, 461, 462

[56] References Cited

U.S. PATENT DOCUMENTS

| | | | |
|---|---|---|---|
| 5,213,811 | 5/1993 | Frisbee et al. | 424/494 |
| 5,229,135 | 7/1993 | Philippon et al. | 424/494 |
| 5,320,853 | 6/1994 | Noda et al. | 424/497 |
| 5,364,620 | 11/1994 | Geoghegan | 424/497 |
| 5,407,686 | 4/1995 | Patel et al. | 424/494 |

*Primary Examiner*—Melvyn I. Marquis
*Assistant Examiner*—Amy Hulina

[57] ABSTRACT

This invention is directed to a multilayered controlled release pharmaceutical dosage form. More particularly the dosage form is adapted for water soluble drugs and comprises a plurality of coated particles wherein each has multiple layers about a core containing a drug active whereby the drug containing core and at least one other layer of drug active is overcoated with a controlled release barrier layer and preferably an outer layer of additional drug is adapted for immediate release to preferably provide one immediate releasing layer and at least two controlled releasing layers of a water soluble drug from the multilayered coated particle.

13 Claims, 1 Drawing Sheet

MULTILAYERED CONTROLLED RELEASE PHARMACEUTICAL DOSAGE FORM

This is a division of application Ser. No. 217,331, filed Mar. 23, 1994, U.S. Pat. No. 5,395,626, which is hereby incorporated by reference.

FIELD OF THE INVENTION

This invention is directed to a multilayered controlled release pharmaceutical dosage form. More particularly, the dosage form is adapted for controlled release of water soluble drugs and comprises a plurality of multilayered coated particles, wherein each particle has multiple layers about a core containing a drug active. The drug containing core and at least one other layer of drug active is overcoated with a controlled release barrier layer and an outer layer of additional drug may be adapted for immediate release.

BACKGROUND OF THE INVENTION

Controlled release pharmaceutical dosage forms are well known and provide distinct advantages for delivery of certain chemotherapies. Controlled release dosage forms are particularly useful for drugs which act optimally at certain levels of plasma concentration over extended periods of time. Controlled release systems may also avoid the presence of ineffective or toxic levels of drugs which result from periodic administration of immediate release dosage forms which provide high initial levels of drug but may leave only ineffectively small amounts of drugs in the plasma near the end of the administration periods (i.e. cycles) prior to subsequent administration of drug. Controlled release dosage forms are also desirable for providing continuous chemotherapy for chronic conditions or those with a long duration of therapy by providing drugs in a sustained released manner that only requires administration either once or twice daily instead of every four to six hours as may be indicated for a particular drug.

The administration of highly water soluble drugs in a controlled release dosage form presents particular problems. The introduction of such highly water soluble drugs in controlled release dosage forms into a patient's digestive system has met with limited success due to the normally unpredictable leaching out of the very water soluble drug active into the digestive system when using conventional sustained release techniques. It is also challenging to provide a substantially zero or constant rate of release for drugs that are highly water soluble for extended periods of time.

It is therefore an object of the present invention to provide a multilayered controlled release pharmaceutical dosage form system, particularly for very water soluble drugs. This system provides desirable plasma levels of drugs with a substantially constant rate of release of the drugs from controlled release layers over a preselected period of time.

SUMMARY OF THE INVENTION

To achieve the objects and objectives in accordance with the invention the present invention provides a multilayered controlled release pharmaceutical dosage form, preferably for water soluble drugs, comprising a plurality of coated particles each comprising: a drug active core which is sequentially overcoated with a first controlled release barrier layer; at least one additional layer containing drug active which is overcoated with an additional controlled release layer; and preferably an outer layer containing drug active which is intended for immediate release; whereby, the amount of drug active in the controlled release barrier material utilized in each coating layer thereof is provided in amounts effective to achieve a desirable plasma level of drug active in a patient over a preselected time period. In particularly preferred embodiments the time period is twelve or twenty-four hours (i.e. corresponding to once or twice daily administration).

In preferred embodiments of the invention the multilayered controlled release pharmaceutical dosage form for water soluble drugs comprises a plurality of coated particles each comprising:

a core comprising an inert material which is coated or granulated with a water soluble drug active;

a first coating layer over the drug containing core comprising a water soluble film forming polymer, preferably the film forming mixture additionally comprises a plasticizer;

a second coating layer over the first coating layer comprising a film forming dispersion or solution which forms a controlled release layer over the coated drug core, preferably a water-based dispersion;

a third coating layer comprising a water soluble film forming polymer and preferably a plasticizer;

a fourth coating layer comprising additional water soluble drug active;

a fifth coating layer comprising a water soluble film forming polymer and preferably a plasticizer;

a sixth coating layer comprising a film forming dispersion or solution which forms a controlled release layer over the coated drug core, preferably a water-based dispersion; and a final coating layer of a water soluble film forming polymer and preferably a plasticizer.

In preferred embodiments of the invention the water soluble film forming polymer is hydroxypropyl methylcellulose and the plasticizer is polyethylene glycol.

Preferably the film forming polymer which forms the controlled release layer is provided as a water-based dispersion and comprises ethyl cellulose. Preferably the dispersion additionally comprises at least one of dibutyl sebacate, oleic acid, and sodium lauryl sulfate.

In preferred embodiments of the invention the water soluble drug active is selected from the group consisting of tramadol, pseudoephedrine and phenylpropanolamine and salts thereof. More preferably the drug active is very water soluble and is tramadol HCl or pseudoephedrine HCl. Most preferably the drug active is tramadol HCl. The invention is also intended to cover substantially pure active enamtiomers of these drug actives.

In a particularly preferred embodiment of the invention the controlled release layers of the second and sixth coating layers are provided at levels to obtain a substantially constant release profile of the drug active over about a twenty-four hour period.

In other embodiments the invention provides a method of achieving a desirable plasma level of a water soluble drug over a twenty-four hour period in a patient comprising the steps of:

preparing a multilayered controlled release dosage form by sequentially overcoating a drug active containing core with a first controlled release barrier layer;

providing at least one additional layer containing drug active over said first controlled release barrier layer which in turn is overcoated by an additional controlled release layer; and providing an outer layer containing drug active which is intended for immediate release; whereby, the amount of drug active and the controlled release barrier material utilized in each coating layer thereof is provided in an amount effective to achieve a desirable plasma level of drug active in a patient over a twenty-four hour period.

In preferred embodiments of the method of the invention the drug is tramadol HCl or pseudoephedrine HCl.

In other preferred embodiments of the method of the invention the sequential coatings are all applied in aqueous systems.

In particularly preferred embodiments of the method of the invention the multilayered dosage form comprises at least one additional coating layer of a water soluble film forming polymer interposed between one or more of the controlled release ! layers and the adjoining layer containing drug active to assure uniformity of the dosage form.

In other embodiments of the invention two or more drug actives may be provided in one or more of the drug containing layers of the multilayered dosage forms.

DETAILED DESCRIPTION OF THE PREFERRED EMBODIMENTS OF THE INVENTION

Figure 1:
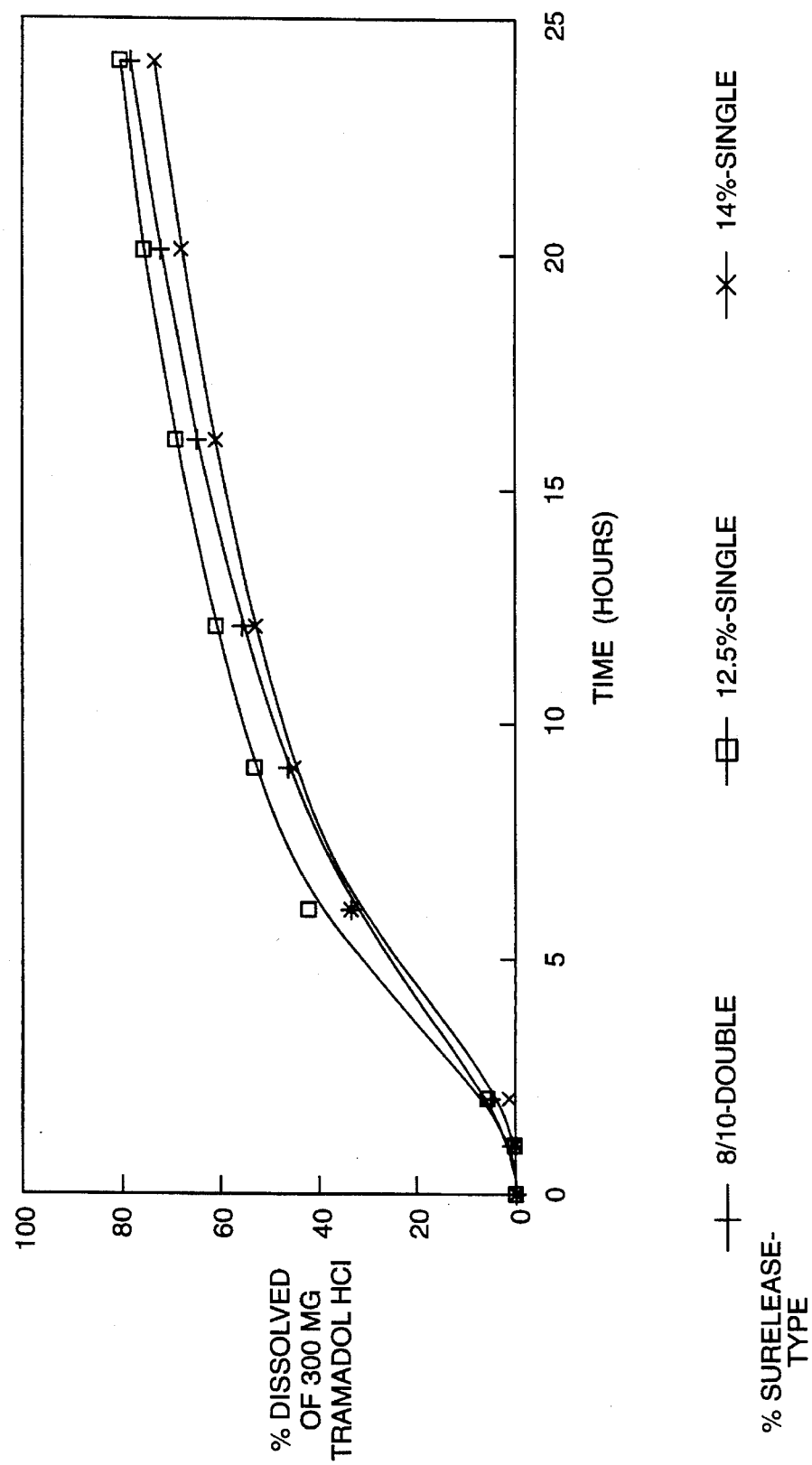
FIG. 1 is a graph showing percent dissolved over time of single and double layer (controlled release layer) coated beads of the drug tramadol HCl.

Reference will now be made in detail to preferred embodiments of the invention. Examples of the preferred embodiments are illustrated in the following example section.

As used herein the term water soluble refers to those compounds and compositions which range from slightly soluble to very soluble in water. Actives which are moderately to highly water soluble are particularly preferred for use in this invention because the multilayered approach taken herein provides barriers to premature leaching of water soluble actives which may, in clinical use, undesirably speed up the rate of release of such actives from conventional sustained release dosage forms. Examples of very or highly water soluble actives include tramadol HCl, pseudoephedrine HCl and phenylpropanolamine HCl.

The multilayered controlled release pharmaceutical dosage form of the invention is well suited for water soluble and very water soluble drugs. The plurality of coating layers including at least two controlled release layers and various sealing layers provide a dosage form which permits effective and desirable controlled release of drug substance from a plurality of coated pellets in a dosage form by providing at least two diffusion barriers through which drug active is slowly released. The multilayered coated particles of the invention are particularly well suited for very water soluble drugs since the multicontrol release barrier approach of the present invention mitigates the possibility of premature leaching out of very water soluble drug active in aqueous systems such as the digestive tract. While the present invention can be used for non-water soluble drugs it is particularly advantageous when applied to more water soluble drugs which are more prone to leaching as described above. The multilayered dosage form may contain more than one drug active in any or all of the drug containing layers thereof.

The drug active core of the multilayered controlled release pharmaceutical dosage form is generally a sugar sphere which is coated with a drug active. This core may however be a combination of a drug active and binder which is granulated into a sphere or the core may be some other non-active substance besides sugar. Each time drug active is provided in a layer it is first overcoated with a water soluble film forming polymer to inhibit the leaching of such drug active during processing into the next applied layer, e.g. controlled release layer. Such leaching into the controlled release layer may have the effect of contaminating the controlled release layer to provide for inconsistent results from layer to layer and/or batch to batch of the drug dosage form because the presence of the leached active would provide for premature release of the active as well as opening up excess space in the controlled release layer for further premature diffusion of the drug active therefrom. The inclusion of such a protective layer over the drug active is particularly indicated in the present invention because of the aqueous nature of the preferred water based polymer controlled release layer which is to be provided over each drug containing core. Further, in cases where the drug is particularly water soluble, undesirable leaching is a probable result absent provision of a protective coating of a water soluble film forming polymer over the drug containing layer.

It is preferred that the water soluble film forming polymer comprises a plasticizer to assure adequate flexibility of the film forming polymer layer. If the film forming polymer layer is comprised of a substance which inherently has adequate flexibility then a plasticizer may not be necessary. The water soluble film forming polymer is preferably hydroxypropyl methylcellulose but may be other suitable polymers such as hydroxypropyl cellulose or povidone and more preferably additionally comprises polyethylene glycol and or propylene glycol as plasticizer. Preferably this polymer is in a liquid solution. Other water soluble polymers may be applied as would be known to those skilled in the art.

The controlled release layer of the multilayered drug dosage form of the invention is a diffusion layer through which drug is released in a controlled manner. It is particularly desirable that the controlled release diffusion layer be water based for ease of processing and environmental concerns. The use of a water based dispersion to form a controlled release layer indicates the use of a protective undercoating as described above to protect against premature leaching of the underlying drug into the subsequently applied controlled release layer which may provide inconsistent release patterns for the drug. While the present invention preferably provides for two controlled released layers; three or more controlled release layers are contemplated and are a part of the present invention. The use of two or more controlled release layers and the underlying drug layers may also provide for customization of the multilayered drug pellets controlled release profile of one drug or for the release of a mixture of drug actives from the pellet.

In preferred embodiments of the invention an immediate release layer of drug is provided on the outside core of the multilayered pellet to provide for the immediate introduction of an effective amount of drug active to a patient. An effective level of drug active is then maintained through the gradual release of additional drug active by diffusion through the controlled release layers of the drug while it remains in the digestive system.

The controlled release layer may be a solution or dispersion of a film forming polymer. Preferably, the controlled release layer is applied as a water based dispersion comprising ethyl cellulose. More preferably, the dispersion additionally comprises plasticizer ingredients such as dibutyl sebacate and oleic acid. A particularly preferred water based controlled release dispersion is sold under the trademark SURELEASE and comprises ethyl cellulose, dibutyl sebacate, oleic acid, ammoniated water, and fused silica.

The multilayered controlled release pellets of the invention are preferably provided in a hard gelatin capsule but may also be provided in any other suitable oral dosage form such as a matrix comprising such pellets agglomerated with an appropriate and compatible binder to form a unitary solid dosage form which will release the intact pellets in the digestive tract after swallowing.

The film forming process of the invention can be carried out in conventional pans, preferably pans with one way air flow to provide more control over the pan environment. More preferably the coating is accomplished in a fluidized bed which is an air suspension technique known as "Wurster" coating. Most preferably the pellets are coated in a rotor granulator with a top fluid bed which provides rotation of the pellets during coating to ensure a more uniform coat of the pellets. Examples of a preferred coating apparatus of the invention is a GLATT GPCG-5 rotor granulator. Other coating materials and techniques can be applied such as those disclosed in *The Theory and Practice of Industrial Pharmacy*, Lachman et al., 3d edition, 1986.

The invention will now be illustrated by examples. The examples are not intended to be limiting of the scope of the present invention but read in conjunction with the detailed and general description above, provide further understanding of the invention and outline a process for preparing the compositions of the inventions and methods of practicing the invention.

EXAMPLES

The following ingredients, processes and procedures for preparing the compositions of the present invention correspond to that described above. The procedure below describes with particularity the various formulation ingredients and procedures utilized. Any methods, starting materials, reagents or excipients which are not particularly described will be generally known and available to those skilled in the pharmaceutical formulation arts. All formulation percentages are provided in percent by weight by total weight of the composition.

Example 1

300 mg. tramadol sustained release capsules

A. Composition: Unit Dose

The theoretical quantitative composition (per unit dose) for tramadol HCl 300 mg sustained release capsules is provided below:

| Components | % weight/weight (theoretical) | mg/Capsule (theoretical) |
|---|---|---|
| Tramadol HCl | 68.34 | 300 |
| (OPADRY ® Clear YS-3-7011)[1] | 1.14 | 5.01 |
| Purified Water, USP[2] | — | — |
| Sugar Spheres, NF | 12.5 | 54.87 |
| OPADRY ® Clear YS-1-7006[3] | 4.48 | 19.66 |
| SURELEASE ® E-7-7050[4] | 13.54 | 59.44 |
| Capsules[5] | — | — |
| Total | 100.00% | 438.98 mg[6] |

[1] A mixture of hydroxypropyl methylcellulose, polyethylene glycol and propylene glycol.
[2] Purified Water, USP is evaporated during processing.
[3] A mixture of hydroxypropyl methylcellulose and polyethylene glycol.
[4] Solid content only of a 25% aqueous dispersion of a mixture of ethyl cellulose, dibutyl sebacate, oleic acid, ammoniated water and fumed silica. The water in the dispersion is evaporated during processing.
[5] White, opaque, hard gelatin capsule, size 00.
[6] Each batch is assayed prior to filling and the capsule weight is adjusted as required to attain 300 mg tramadol hydrochloride per capsule.

The quantative batch composition for tramadol hydrochloride 300 mg sustained release capsule is shown below (Theoretical batch quantity 25,741 capsules):

| Components | Weight |
|---|---|
| Step 1: Preparation of Tramadol Hydrochloride Beads (bead Build-up #1) | |
| Tramadol Hydrochloride | 12.000 |
| Opadry ® Clear YS-3-7011 | 0.200 |
| Purified Water, USP | 5.454 |
| Sugar Spheres, NF | 4.000 |
| Total Weight Tramadol Hydrochloride Beads (Bead Build-up #1) | 16.200 kg |
| Step 2: Clear & Sustained Release Bead Coating #1 | |
| Tramadol Hydrochloride Beads (derived from Step 1) | 8.000 |
| Opadry ® Clear YS-1-7006 | 0.360 |
| Purified Water, USP | 5.928 |
| Surelease ® E-7-7050 | 0.672 |
| Total Weight Clear Coated Sustained Release Beads | 9.032 kg |
| Step 3: Tramadol Hydrochloride Beads (Build-up #2) | |
| Sustained Release Beads (derived from Step 2) | 8.000 |
| Tramadol Hydrochloride | 4.320 |
| Opadry ® Clear YS-3-7011 | 0.072 |
| Purified Water, USP | 1.964 |
| Total Weight Tramadol Hydrochloride Beads (Build-up #2) | 12.392 kg |
| Step 4: Clear & Sustained Release Bead Coating #2 | |
| Tramadol Hydrochloride Beads (derived from Step 3) | 10.000 |
| Opadry ® Clear YS-1-7006 | 0.250 |
| Purified Water, USP | 6.450 |
| Surelease ® E-7-7050 | 1.050 |
| Total Weigh Tramadol Hydrochloride Sustained Release Beads | 11.300 kg |
| Step 5: Capsule Filling | — |

B. Methods of Manufacturing and Packaging

NOTE: The drug substance and excipients may be deagglomerated, if needed, by milling or screening.

Step 1: Preparation of Tramadol Hydrochloride Beads (Bead Build-up #1)

a. Preparation of Tramadol Hydrochloride Build-up Solution
  i. Admix the batch quantity of Purified Water, USP and the batch quantity of Opadry® Clear YS-3-7011.

ii. Add the batch quantity of tramadol hydrochloride and mix for approximately 1.5 hours.

b. Preparation of Tramadol Hydrochloride Beads i. Load the bowl of a suitable bead coater such as the Glatt GPCG 5 Rotor-Granulator with the batch quantity of sugar spheres, NF and heat until the bed reaches approximately 40° C.–60° C.

ii. While maintaining the bed temperature at approximately 40°–60° C., spray the entire tramadol hydrochloride/Opadry® Clear YS-3 -7011 solution prepared in Step 1.a. onto the sugar spheres.

iii. Remove the tramadol hydrochloride beads from the granulator and screen to remove any agglomerates and any fine powder.

Step 2: Clear and Sustained Release Bead Coating #1 a. Preparation of Clear Coat #1

Add 54.7% of the batch quantity of Purified Water, USP (3.240 kg) and the batch quantity of Opadry® Clear YS-1-7006 (0.360 kg) and mix for approximately 1–2 hours.

b. Preparation of Sustained Release Dispersion #1

Add 11.3% of the batch quantity of Purified Water, USP (0.672 kg) and 2.688 kg of Surelease® E-7-7050 dispersion and mix for approximately 1–2 hours.

c. Preparation of Coated Beads i. Transfer the batch quantity of the tramadol hydrochloride beads prepared in Step 1. (8.0 kg) into a suitable bead coater such as the Glatt GPCG 5 Rotor-Granulator and heat until the bed reaches approximately 40° C.–60° C.

ii. Maintain the bed temperature at the following conditions and spray:

40° C.–60° C. 88.9% of the Opadry® Clear YS-1 -7006 solution prepared in Step 2.a.

42° C.–50° C. the batch quantity of the Surelease® E-7-7050 dispersion prepared in Step 2.b.

40° C.–60° C. the remaining batch quantity (11.1%) of the Opadry® Clear YS-1-7006 solution prepared in Step 2.a.

iii. Remove the tramadol sustained release beads derived in Step 2.c.ii. from the granulator and screen the beads to remove any agglomerates and any remaining fine powder.

Step 3: Tramadol Hydrochloride Beads (Build-up #2)

a. Preparation of the Tramadol Hydrochloride Build-up Solution i. Add the batch quantity of Purified Water, USP and the batch quantity of Opadry® Clear YS-3-7011.

ii. Add the batch quantity of tramadol hydrochloride and mix for approximately 1–2 hours.

b. Preparation of the Tramadol Hydrochloride Beads i. Load the bowl of a suitable bead coater such as the Glatt GPCG 5 Rotor-Granulator with the batch quantity of sustained release beads from Step 2. (8.0 kg) and heat until the bed reaches approximately 40° C.–60° C.

ii. Spray on the entire tramadol hydrochloride/Opadry® Clear YS-3-7011 solution prepared in Step 3.a. onto the heated sustained release beads, while maintaining the bed temperature at approximately 40° C.–60° C.

iii. Remove the tramadol hydrochloride beads from the granulator and screen the beads to remove any agglomerates and any fine powder.

Step 4: Clear and Sustained Release Bead Coating #2 a. Preparation of Clear Coat

Add 34.9% of the respective batch quantity of Purified Water, USP (2.250 kg) and the respective batch quantity of Opadry® Clear YS-1 -7006 (0.250 kg) and mix for approximately 1–2 hours.

b. Preparation of Sustained Release Dispersion #2

Add to a suitable stainless steel mixing tank 16.3% of the batch quantity of Purified Water, USP (1.050 kg) and 4.200 kg of Surelease® E-7 -7050 dispersion and mix for approximately 1–2 hours.

c. Preparation of Coated Beads i. Transfer the batch quantity of the tramadol hydrochloride beads prepared in Step 3. (10.0 kg) into a suitable granulator such as the Glatt GPCG 5 Rotor-Granulator and heat until the bed reaches approximately 40° C.–60° C.

ii. Maintain the bed temperature at the following conditions and sprays:

40° C.–60° C. 80% of the Opadry® Clear YS-1 -7006 solution prepared in Step 4.a.

42° C.–50° C. the batch quantity of the Surelease® E-7-7050 dispersion prepared in Step 4.b.

40° C.–60° C. the remaining batch quantity (20.0%) of the Opadry® Clear YS-1-7006 solution prepared in Step 4.a.

iii. Remove the tramadol sustained release beads derived in Step 4.c.ii. from the granulator and screen the beads to remove any agglomerates and any remaining fine powder.

iv. Dry the beads in a 45° C.–55° C. dry heat oven for approximately 24 hours.

Step 5: Capsule Filing a. Based on the in-process assay results, calculate the fill weight of the tramadol hydrochloride sustained release beads.

b. On a suitable filling machine or by hand, fill the calculated amount of tramadol hydrochloride sustained release beads into white, opaque, hard gelatin capsules (size 00).

Example 2

Preparation of Pseudophedrine sustained Release Capsules

Follow the procedure of Example 1 but replace the tramadol HCl with pseudophedrine HCl and reduce all of the ingredients to two-thirds to produce 200 mg pseudophedrine sustained release capsules.

The present invention provides for a heretofore unrealized consistent drug release pattern for very water soluble drugs such as tramadol HCl and pseudophedrine HCl from a sustained released pellet system. The advantages obtained by the multilayered pellets of the invention are indicated in the appended graph of FIG. 1 for comparing formulations for tramadol, The graph shows that the double layer bead of the invention (i.e. two controlled release layers, i.e. 8% and 10% controlled release layer amounts, by weight of the total weight of the beads) provides a more linear (i.e., more constant or uniform) release rate as compared to single layered beads with a single controlled release layer (i.e., 12.5% and 14% controlled release layer amounts by weight of the total weight of the beads).

The scope of the present invention is not limited by the description, examples or suggested uses herein and modifications can be made without departing from the spirit of the invention. The multilayered dosage forms of the invention may, for example, have other applications and uses in addition to those described herein, e.g. for vitamin supplements or for controlled delivery of diagnostic agents.

Applications of the compositions and methods of the present invention for medical or pharmaceutical uses can be accomplished by any clinical, medical, and pharmaceutical methods and techniques as are presently or prospectively known to those skilled in the art. Thus it is intended that the invention cover any modifications and variations of this invention provided that they come within the scope of the appended claims and their equivalents.

What is claimed is:

1. A multilayered controlled release pharmaceutical dosage form for water soluble drugs comprising a plurality of coated particles each comprising:

a core comprising an inert material which is coated or granulated with a water soluble drug active;

a first coating layer over the drug containing core comprising a water soluble film forming polymer;

a second coating layer over the first coating layer comprising a dispersion of a film forming polymer which forms a controlled release layer over the coated drug core;

a third coating layer comprising a water soluble film forming polymer;

a fourth coating layer comprising additional water soluble drug active;

a fifth coating layer comprising a film forming mixture of a water soluble film forming polymer;

a sixth coating layer comprising a dispersion of a film forming polymer which forms a controlled release layer over the coated drug core; and a final coating layer of a water soluble film forming polymer.

2. The multilayer dosage form of claim 1 wherein at least one of the coating layers of water soluble film forming polymer additionally comprises a plasticizer.

3. The multilayer dosage form of claim 1 additionally comprising an outer layer of water soluble drug active intended for substantially immediate release.

4. The multilayer dosage form of claim 1 wherein the water soluble film forming polymer is selected from the group consisting of hydroxypropyl methylcellulose, hydroxypropyl cellulose and povidone.

5. The multilayered dosage form of claim 2 wherein the plasticizer is polyethylene glycol.

6. The multilayered dosage form of claim 1 wherein the dispersion of the film forming polymer which forms a controlled release layer is water based.

7. The multilayered dosage form of claim 1 wherein the water soluble drug active is selected from the group consisting of tramadol, pseudoephedrine, phenylpropanolamine and salts thereof.

8. The multilayered dosage form of claim 1 wherein the drug active is very water soluble and is tramadol HCl or pseudoephedrine HCl.

9. The multilayered dosage form of claim 1 wherein the drug active is tramadol HCl.

10. The multilayered dosage form of claim 6 wherein the film forming polymer is ethyl cellulose.

11. The multilayered dosage form of claim 10 wherein the dispersion of the film forming polymer which forms a controlled release layer additionally comprises at least one of dibutyl sebacate or oleic acid.

12. The multilayered dosage form of claim 1 wherein the total amounts of drug active provided in each of the drug containing layers are selected to achieve a desirable plasma level of drug active over about a twenty-four hour period.

13. The multilayered dosage form of claim 1 wherein two or more different drug activities are provided in one or more drug layers.

* * * * *